(12) United States Patent
Olson

(10) Patent No.: US 12,059,676 B1
(45) Date of Patent: *Aug. 13, 2024

(54) DEVICE AND METHOD FOR TESTING SERUM AND PLASMA SEPARATED FROM BLOOD CELLS IN WHOLE BLOOD SAMPLES

(71) Applicant: Babson Diagnostics, Inc., Austin, TX (US)

(72) Inventor: Eric Olson, Austin, TX (US)

(73) Assignee: Babson Diagnostics, Inc., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/511,683

(22) Filed: Nov. 16, 2023

Related U.S. Application Data

(63) Continuation of application No. 18/323,830, filed on May 25, 2023, which is a continuation of application No. 17/082,759, filed on Oct. 28, 2020, now Pat. No. 11,697,114, which is a continuation of application No. 16/061,309, filed as application No. PCT/US2016/066236 on Dec. 12, 2016, now Pat. No. 10,870,110.

(60) Provisional application No. 62/266,433, filed on Dec. 11, 2015.

(51) Int. Cl.
*B01L 3/00* (2006.01)

(52) U.S. Cl.
CPC ....... *B01L 3/5021* (2013.01); *B01L 2300/042* (2013.01)

(58) Field of Classification Search
CPC ..... B01D 21/26; B01D 21/262; B01L 3/5021; B01L 3/50215; B01L 2400/0409; G01N 1/4077; G01N 21/07

See application file for complete search history.

(56) References Cited

U.S. PATENT DOCUMENTS

| 1,892,884 A | 1/1933 | Grauman et al. |
| 2,110,237 A | 3/1938 | Parsons |
| 2,240,101 A | 4/1941 | Fred et al. |
| 2,722,257 A | 11/1955 | Lockhart |
| 2,775,350 A | 12/1956 | Jones |

(Continued)

FOREIGN PATENT DOCUMENTS

| CA | 2058917 A1 | 7/1993 |
| CN | 1501080 A | 6/2004 |

(Continued)

OTHER PUBLICATIONS

Co-pending U.S. Appl. No. 17/818,169, inventor Olson; Eric, filed Aug. 8, 2022.

(Continued)

*Primary Examiner* — Jill A Warden
*Assistant Examiner* — Dwayne K Handy

(57) ABSTRACT

A device and method for separating serum or plasma from blood cells in a whole blood specimen. The present invention uses a cap with a reservoir, such that blood cells are packed into the cap when the specimen container is centrifuged. When the cap is removed, the blood cells are also removed, and the serum or plasma is left in the specimen tube where it can be readily extracted by a pipette which is able to reach all the way to the bottom of the specimen tube minimizing the dead volume.

23 Claims, 6 Drawing Sheets

(56) References Cited

U.S. PATENT DOCUMENTS

| | | |
|---|---|---|
| 2,896,502 A | 7/1959 | Nordin |
| 2,912,895 A | 11/1959 | Houston et al. |
| 3,081,029 A | 3/1963 | Kjetil et al. |
| 3,300,051 A | 1/1967 | Mitchell |
| 3,326,400 A | 6/1967 | Jacques et al. |
| 3,419,179 A | 12/1968 | Fritz et al. |
| 3,420,107 A | 1/1969 | Rowett et al. |
| 3,434,859 A | 3/1969 | Benjamin et al. |
| 3,478,889 A | 11/1969 | Fessler et al. |
| 3,481,712 A | 12/1969 | Bernstein et al. |
| 3,508,653 A | 4/1970 | Coleman et al. |
| 3,525,254 A | 8/1970 | Milanes et al. |
| 3,539,300 A | 11/1970 | Stone et al. |
| 3,611,403 A | 10/1971 | Gilford et al. |
| 3,615,222 A | 10/1971 | Mead |
| 3,626,929 A | 12/1971 | Sanz et al. |
| 3,654,925 A | 4/1972 | Holderith |
| 3,684,455 A | 8/1972 | Vacirca et al. |
| 3,701,434 A | 10/1972 | Moore |
| 3,706,305 A | 12/1972 | Berger et al. |
| 3,706,306 A | 12/1972 | Berger et al. |
| 3,733,179 A | 5/1973 | Guehler et al. |
| 3,750,645 A | 8/1973 | Bennett et al. |
| 3,761,408 A | 9/1973 | Jae et al. |
| 3,768,979 A | 10/1973 | Mead et al. |
| 3,780,935 A | 12/1973 | Lukacs et al. |
| 3,786,985 A | 1/1974 | Blaivas |
| 3,814,248 A | 6/1974 | Lawhead |
| 3,818,188 A | 6/1974 | Hertel et al. |
| 3,849,072 A | 11/1974 | Ayres |
| 3,852,194 A | 12/1974 | Zine, Jr. |
| 3,862,042 A | 1/1975 | Ayres |
| 3,879,295 A | 4/1975 | Glover et al. |
| 3,920,549 A | 11/1975 | Gigliello et al. |
| 3,926,521 A | 12/1975 | Ginzel |
| 3,928,139 A | 12/1975 | Dorn |
| 3,929,646 A | 12/1975 | Adler |
| 3,931,010 A | 1/1976 | Ayres et al. |
| 3,938,953 A | 2/1976 | Paschalis et al. |
| 3,939,822 A | 2/1976 | Markowitz |
| 3,942,717 A | 3/1976 | Robison |
| 3,958,944 A | 5/1976 | Wong |
| 3,972,812 A | 8/1976 | Gresl, Jr. |
| 3,985,649 A | 10/1976 | Eddelman |
| 3,999,868 A | 12/1976 | Sanz et al. |
| 4,012,325 A | 3/1977 | Columbus |
| 4,046,699 A | 9/1977 | Zine, Jr. |
| 4,050,451 A | 9/1977 | Columbus |
| 4,052,320 A | 10/1977 | Jakubowicz |
| 4,055,501 A | 10/1977 | Cornell |
| D246,800 S | 12/1977 | Wong |
| 4,081,356 A | 3/1978 | Zierdt |
| 4,083,788 A | 4/1978 | Ferrara |
| 4,088,582 A | 5/1978 | Murty et al. |
| 4,092,113 A | 5/1978 | Hardy |
| 4,131,512 A | 12/1978 | Dorn |
| 4,131,549 A | 12/1978 | Ferrara |
| 4,132,225 A | 1/1979 | Whattam |
| 4,136,036 A | 1/1979 | Columbus |
| 4,147,628 A | 4/1979 | Bennett et al. |
| 4,154,690 A | 5/1979 | Ballies |
| 4,164,449 A | 8/1979 | Dorn et al. |
| 4,169,060 A | 9/1979 | Columbus |
| 4,180,465 A | 12/1979 | Murty |
| 4,227,620 A | 10/1980 | Conway |
| 4,235,725 A | 11/1980 | Semersky |
| 4,257,886 A | 3/1981 | Kessler |
| 4,294,707 A | 10/1981 | Ikeda et al. |
| 4,295,974 A | 10/1981 | Cornell |
| 4,308,232 A | 12/1981 | Crouther et al. |
| 4,358,425 A | 11/1982 | Finney et al. |
| 4,369,117 A | 1/1983 | White |
| 4,417,981 A | 11/1983 | Nugent |
| 4,425,235 A | 1/1984 | Cornell et al. |
| 4,426,290 A | 1/1984 | Ichikawa et al. |
| 4,443,408 A | 4/1984 | Mintz |
| 4,513,522 A | 4/1985 | Selenke |
| 4,591,486 A | 5/1986 | Eberle |
| 4,671,939 A | 6/1987 | Mintz |
| 4,678,559 A | 7/1987 | Szabados |
| 4,735,904 A | 4/1988 | Starr |
| 4,755,356 A | 7/1988 | Robbins et al. |
| 4,762,798 A | 8/1988 | Deutsch |
| 4,775,626 A | 10/1988 | Armenta et al. |
| 4,799,358 A | 1/1989 | Knopf et al. |
| 4,805,772 A | 2/1989 | Shaw et al. |
| 4,811,866 A | 3/1989 | Golias |
| 4,832,678 A | 5/1989 | Sheeran |
| 4,957,707 A | 9/1990 | Hofelich et al. |
| 5,019,243 A | 5/1991 | McEwen et al. |
| 5,030,341 A | 7/1991 | McEwen et al. |
| 5,090,420 A | 2/1992 | Nielsen |
| 5,103,651 A | 4/1992 | Coelho et al. |
| 5,104,533 A | 4/1992 | Szabados |
| 5,151,184 A | 9/1992 | Ferkany |
| 5,236,604 A | 8/1993 | Fiehler |
| 5,275,731 A | 1/1994 | Jahn |
| 5,290,703 A | 3/1994 | Hsu et al. |
| 5,316,146 A | 5/1994 | Graff |
| 5,352,410 A | 10/1994 | Hansen et al. |
| 5,501,841 A | 3/1996 | Lee et al. |
| 5,556,544 A | 9/1996 | Didier |
| 5,614,236 A | 3/1997 | Klang |
| 5,632,905 A | 5/1997 | Haynes |
| 5,665,309 A | 9/1997 | Champseix et al. |
| 5,683,659 A | 11/1997 | Hovatter |
| 5,830,154 A | 11/1998 | Goldstein et al. |
| 5,882,318 A | 3/1999 | Boyde |
| 5,882,943 A | 3/1999 | Aldeen |
| 5,975,313 A | 11/1999 | Sarstedt |
| 6,043,878 A | 3/2000 | Gratzl et al. |
| 6,132,353 A | 10/2000 | Winkelman et al. |
| 6,171,261 B1 | 1/2001 | Niermann et al. |
| 6,221,655 B1 | 4/2001 | Fung et al. |
| 6,234,948 B1 | 5/2001 | Yavilevich |
| 6,270,728 B1 | 8/2001 | Wijnschenk et al. |
| 6,296,763 B1 | 10/2001 | Hicks |
| 6,344,331 B1 | 2/2002 | Ball et al. |
| 6,471,069 B2 | 10/2002 | Lin et al. |
| 6,497,325 B1 | 12/2002 | DiCesare et al. |
| 6,730,071 B1 | 5/2004 | Dassa |
| 6,793,885 B1 | 9/2004 | Yokoi et al. |
| 7,176,034 B2 | 2/2007 | Efthimiadis et al. |
| 7,638,342 B2 | 12/2009 | Samsoondar |
| 7,736,593 B2 | 6/2010 | Dastane et al. |
| 8,343,426 B2 | 1/2013 | Song |
| 8,550,273 B2 | 10/2013 | Levin et al. |
| 8,632,740 B2 | 1/2014 | Dastane et al. |
| 8,852,505 B2 | 10/2014 | Dupoteau et al. |
| 9,251,393 B2 | 2/2016 | Pollack |
| 9,279,760 B2 | 3/2016 | Imazu et al. |
| 9,488,563 B2 | 11/2016 | Halverson et al. |
| 9,604,219 B2 | 3/2017 | Mortillaro et al. |
| 10,336,539 B2 | 7/2019 | Caveney et al. |
| 10,870,110 B2* | 12/2020 | Olson ............. G01N 21/07 |
| 11,697,114 B2* | 7/2023 | Olson ............. B01D 21/26 |
| | | 436/45 |
| 2001/0025818 A1 | 10/2001 | Warner |
| 2002/0040872 A1 | 4/2002 | Bogoev et al. |
| 2002/0066712 A1 | 6/2002 | Brockwell |
| 2002/0155619 A1 | 10/2002 | Kurihara et al. |
| 2003/0091701 A1 | 5/2003 | Yahav |
| 2003/0209091 A1 | 11/2003 | Fattinger et al. |
| 2004/0005246 A1 | 1/2004 | Efthimiadis et al. |
| 2004/0059255 A1 | 3/2004 | Manoussakis et al. |
| 2004/0129631 A1 | 7/2004 | Anraku et al. |
| 2005/0014273 A1 | 1/2005 | Dahm et al. |
| 2005/0059163 A1 | 3/2005 | Dastane et al. |
| 2005/0123444 A1 | 6/2005 | Tomasso et al. |
| 2005/0132775 A1 | 6/2005 | Laugharn, Jr. et al. |
| 2006/0009713 A1 | 1/2006 | Flaherty |
| 2006/0142669 A1 | 6/2006 | Morimoto et al. |
| 2006/0168985 A1 | 8/2006 | Gano |
| 2007/0020629 A1 | 1/2007 | Ross et al. |

(56) References Cited

U.S. PATENT DOCUMENTS

| | | |
|---|---|---|
| 2007/0048185 A1 | 3/2007 | Dupoteau et al. |
| 2007/0073187 A1 | 3/2007 | Thomson et al. |
| 2007/0083131 A1 | 4/2007 | Escutia et al. |
| 2007/0110627 A1 | 5/2007 | Nagai et al. |
| 2007/0231834 A1 | 10/2007 | Hale |
| 2008/0003148 A1 | 1/2008 | Dause |
| 2008/0096282 A1 | 4/2008 | Samsoondar |
| 2008/0185349 A1 | 8/2008 | Willliams |
| 2008/0213377 A1 | 9/2008 | Bhatia et al. |
| 2008/0237115 A1 | 10/2008 | Shintani et al. |
| 2008/0286150 A1 | 11/2008 | Pankow |
| 2008/0313877 A1 | 12/2008 | Campbell |
| 2009/0257922 A1 | 10/2009 | Baker |
| 2010/0062415 A1 | 3/2010 | Schwoebel et al. |
| 2010/0111773 A1 | 5/2010 | Pantelidis |
| 2010/0114056 A1 | 5/2010 | Nagai |
| 2010/0261988 A1 | 10/2010 | Tamir |
| 2010/0288060 A1 | 11/2010 | Ronsick et al. |
| 2010/0294050 A1 | 11/2010 | Massaro |
| 2010/0297659 A1 | 11/2010 | Yoo |
| 2010/0303688 A1 | 12/2010 | Andersen |
| 2011/0263408 A1 | 10/2011 | Suto et al. |
| 2012/0048002 A1 | 3/2012 | Mallet |
| 2012/0048827 A1 | 3/2012 | Levin |
| 2012/0053041 A1 | 3/2012 | Ihm et al. |
| 2012/0058027 A1 | 3/2012 | Song |
| 2012/0258531 A1 | 10/2012 | Seubert et al. |
| 2013/0045477 A1 | 2/2013 | Harder et al. |
| 2013/0045852 A1 | 2/2013 | Chapman et al. |
| 2013/0125628 A1 | 5/2013 | Kitagawa et al. |
| 2013/0167768 A1 | 7/2013 | Smith et al. |
| 2013/0209985 A1 | 8/2013 | Hoke et al. |
| 2013/0224851 A1 | 8/2013 | Ljungmann et al. |
| 2013/0280130 A1 | 10/2013 | Sarwar et al. |
| 2013/0323711 A1 | 12/2013 | Singh et al. |
| 2014/0065018 A1 | 3/2014 | Imazu et al. |
| 2014/0073990 A1 | 3/2014 | Holmes et al. |
| 2014/0096598 A1 | 4/2014 | Halverson et al. |
| 2014/0105796 A1 | 4/2014 | Nagy |
| 2014/0113278 A1 | 4/2014 | Thomas et al. |
| 2014/0241957 A1 | 8/2014 | Serhan et al. |
| 2014/0255254 A1 | 9/2014 | Yamaguchi et al. |
| 2014/0273242 A1 | 9/2014 | Ochranek et al. |
| 2014/0296089 A1 | 10/2014 | Holmes et al. |
| 2014/0356254 A1 | 12/2014 | Lee et al. |
| 2014/0374480 A1 | 12/2014 | Pollack |
| 2015/0018715 A1 | 1/2015 | Walterspiel |
| 2015/0056716 A1 | 2/2015 | Oyler et al. |
| 2015/0072346 A1 | 3/2015 | Gellibolian et al. |
| 2015/0111299 A1 | 4/2015 | Watabe et al. |
| 2015/0151294 A1 | 6/2015 | Cho et al. |
| 2015/0289856 A1 | 10/2015 | Saqi et al. |
| 2015/0316532 A1 | 11/2015 | Makino et al. |
| 2016/0018427 A1 | 1/2016 | Streibl et al. |
| 2016/0097049 A1 | 4/2016 | Qian |
| 2016/0271015 A1 | 9/2016 | Wengreen et al. |
| 2018/0028102 A1 | 2/2018 | George et al. |
| 2018/0259251 A1 | 9/2018 | Poorte et al. |
| 2018/0326413 A1 | 11/2018 | Walkowiak et al. |
| 2018/0353952 A1 | 12/2018 | Olson |
| 2019/0072578 A1 | 3/2019 | Buschke |
| 2019/0145688 A1 | 5/2019 | Tsuno |
| 2019/0320960 A1 | 10/2019 | Olson et al. |
| 2019/0331703 A1 | 10/2019 | Olson et al. |
| 2019/0350808 A1 | 11/2019 | Olson et al. |
| 2020/0150005 A1 | 5/2020 | Slutter et al. |
| 2020/0261308 A1 | 8/2020 | Zhou |
| 2020/0363116 A1 | 11/2020 | Van Bokkelen et al. |
| 2021/0015699 A1 | 1/2021 | Zou et al. |
| 2021/0039088 A1 | 2/2021 | Olson |
| 2021/0063062 A1 | 3/2021 | Alexander et al. |
| 2021/0123936 A1 | 4/2021 | Swanson et al. |
| 2022/0049890 A1 | 2/2022 | Alexander et al. |
| 2022/0117778 A1 | 4/2022 | Knotts |
| 2022/0349910 A1 | 11/2022 | Silbert et al. |
| 2023/0074188 A1 | 3/2023 | Luo et al. |
| 2023/0324425 A1 | 10/2023 | Flanagan et al. |
| 2024/0042427 A1 | 2/2024 | Olson |

FOREIGN PATENT DOCUMENTS

| | | |
|---|---|---|
| CN | 1690714 A | 11/2005 |
| CN | 1826530 A | 8/2006 |
| CN | 1856366 A | 11/2006 |
| CN | 1863495 A | 11/2006 |
| CN | 101311700 A | 11/2008 |
| CN | 101312689 A | 11/2008 |
| CN | 101454665 A | 6/2009 |
| CN | 101678931 A | 3/2010 |
| CN | 201454557 U | 5/2010 |
| CN | 102033007 A | 4/2011 |
| CN | 102209896 A | 10/2011 |
| CN | 102764133 A | 11/2012 |
| CN | 102933949 A | 2/2013 |
| CN | 103123317 A | 5/2013 |
| CN | 103308376 A | 9/2013 |
| CN | 103354765 A | 10/2013 |
| CN | 103393427 A | 11/2013 |
| CN | 103608658 A | 2/2014 |
| CN | 103674672 A | 3/2014 |
| CN | 104034672 A | 9/2014 |
| CN | 104107054 A | 10/2014 |
| CN | 203965173 U | 11/2014 |
| CN | 104768516 A | 7/2015 |
| CN | 105600468 A | 5/2016 |
| CN | 108743197 A | 11/2018 |
| CN | 114159058 A | 3/2022 |
| EP | 0494845 A1 | 7/1992 |
| EP | 1005910 A2 | 6/2000 |
| EP | 1161923 A1 | 12/2001 |
| EP | 1542020 A2 | 6/2005 |
| EP | 1884188 A1 | 2/2008 |
| EP | 2726842 A1 | 5/2014 |
| EP | 3603813 A2 | 2/2020 |
| EP | 3888721 A1 | 10/2021 |
| FR | 2582013 A1 | 11/1986 |
| JP | S4851686 A | 7/1973 |
| JP | S4841632 B1 | 12/1973 |
| JP | H03181852 A | 8/1991 |
| JP | H0526883 A | 2/1993 |
| JP | H0821839 A | 1/1996 |
| JP | H09166591 A | 6/1997 |
| JP | H1033507 A | 2/1998 |
| JP | H10243940 A | 9/1998 |
| JP | H10277019 A | 10/1998 |
| JP | H1183864 A | 3/1999 |
| JP | H11318870 A | 11/1999 |
| JP | 2000084389 A | 3/2000 |
| JP | 2001502595 A | 2/2001 |
| JP | 2001264344 A | 9/2001 |
| JP | 2007503580 A | 2/2007 |
| JP | 2007271388 A | 10/2007 |
| JP | 2008506128 A | 2/2008 |
| JP | 2008099991 A | 5/2008 |
| JP | 2008191070 A | 8/2008 |
| JP | 2009507237 A | 2/2009 |
| JP | 2009089759 A | 4/2009 |
| JP | 2012527613 A | 11/2012 |
| JP | 2014048112 A | 3/2014 |
| JP | 2014173904 A | 9/2014 |
| JP | 2015509202 A | 3/2015 |
| WO | WO-8505048 A1 | 11/1985 |
| WO | WO-9839650 A1 | 9/1998 |
| WO | WO-0170403 A1 | 9/2001 |
| WO | WO-2005014173 A1 | 2/2005 |
| WO | WO-2008027319 A2 | 3/2008 |
| WO | WO-2008119947 A1 | 10/2008 |
| WO | WO-2013003308 A1 | 1/2013 |
| WO | WO-2014050021 A1 | 4/2014 |
| WO | WO-2017100798 A1 | 6/2017 |
| WO | WO-2018090023 A1 | 5/2018 |
| WO | WO-2018090027 A1 | 5/2018 |

(56) References Cited

FOREIGN PATENT DOCUMENTS

WO    WO-2018090030 A2    5/2018
WO    WO-2019006349 A1    1/2019
WO    WO-2023196922 A1   10/2023

OTHER PUBLICATIONS

European Search Report for EP Application No. 20209543 dated Jun. 9, 2021, 1-9.
Non Final Rejection for U.S. Appl. No. 17/082,759, mailed on Oct. 18, 2022, 17 pages.
Non-Final Office Action for U.S. Appl. No. 18/511,683 dated Mar. 1, 2024, 7 pages.
Office Action and English Translation for CN Application No. 201680081591.7, dated Sep. 1, 2020, 20 pages.
Office Action for Chinese Application No. 202110946196, mailed Jun. 22, 2022, 33 pages.
Office Action for Chinese Application No. CN202110946196 dated Mar. 7, 2023, 14 pages.
PCT Written Opinion and Search Report for International Application No. PCT/US2016/066236, dated Mar. 3, 2017, 7 pages.
Non-Final Office Action for U.S. Appl. No. 18/323,830 dated Mar. 28, 2024, 15 pages.
Office Action for European Application No. EP20200209543 dated May 31, 2024, 6 pages.

\* cited by examiner

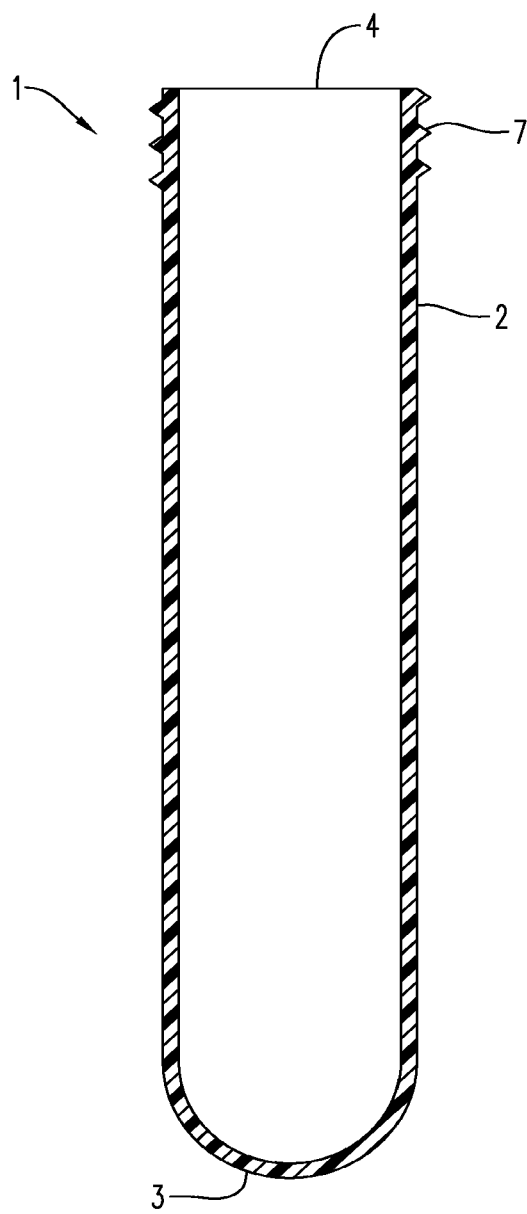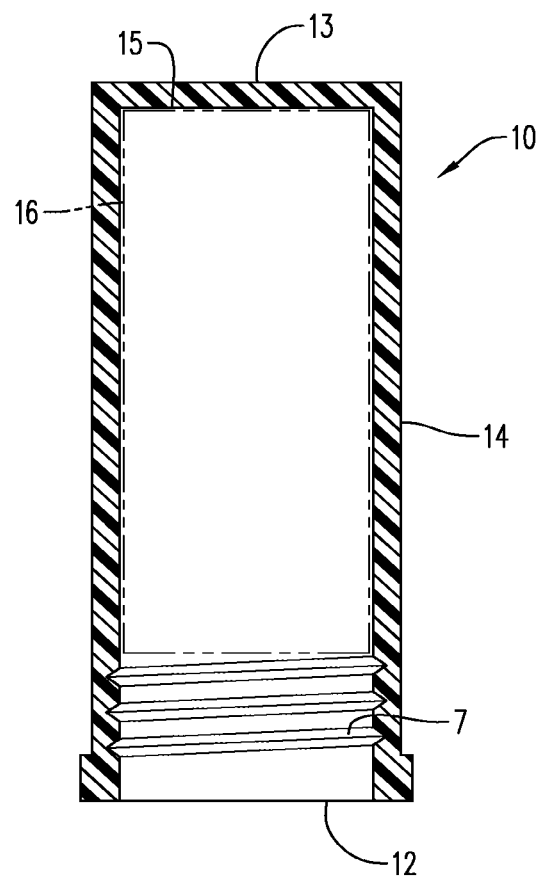
FIG. 1A
FIG. 1B

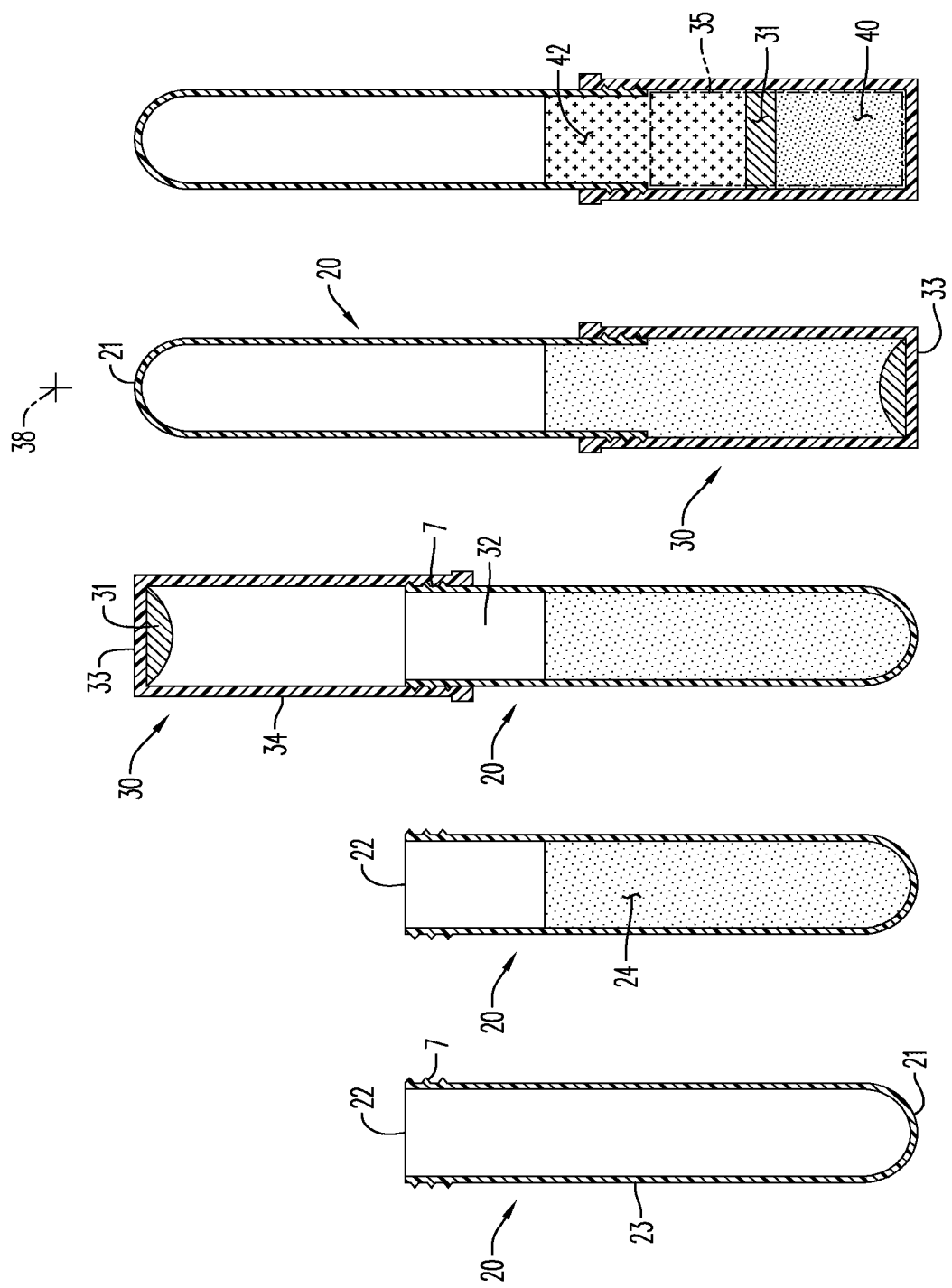

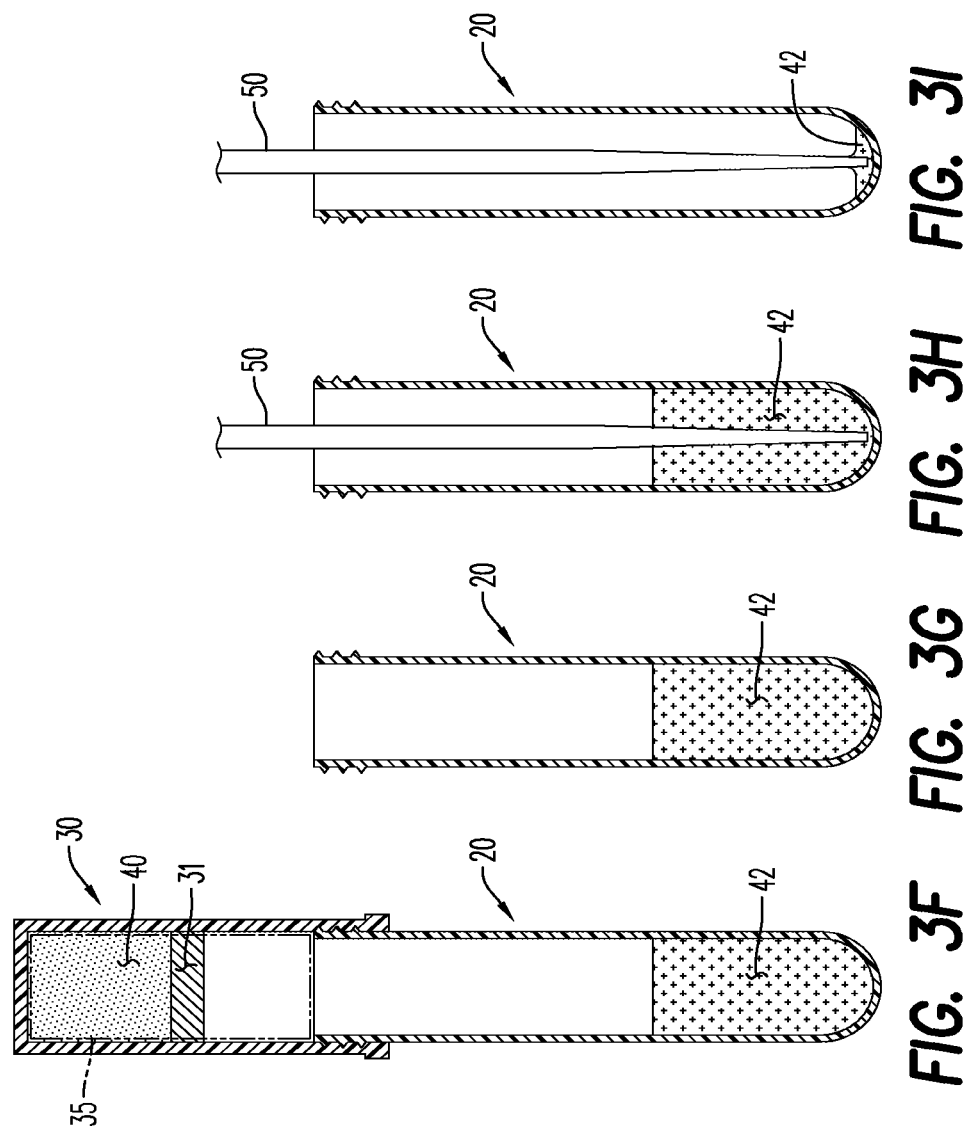

DEVICE AND METHOD FOR TESTING SERUM AND PLASMA SEPARATED FROM BLOOD CELLS IN WHOLE BLOOD SAMPLES

CROSS-REFERENCE TO RELATED APPLICATIONS

This application is a Continuation of U.S. patent application Ser. No. 18/323,830, filed on May 25, 2023, which is a Continuation of U.S. patent application Ser. No. 17/082,759, filed on Oct. 28, 2020, now U.S. Pat. No. 11,697,114, which is a Continuation of U.S. patent application Ser. No. 16/061,309, filed on Jun. 11, 2018, now U.S. Pat. No. 10,870,110, which is a U.S. National Phase Application filed under 35 U.S.C. § 371 of International Application No. PCT/US2016/066236, filed on Dec. 12, 2016, which claims priority to and the benefit of U.S. Provisional Application No. 62/266,433, filed on Dec. 11, 2015, the contents of which are hereby incorporated by reference in their entireties.

TECHNICAL FIELD

The present invention relates to a device and method for separating serum or plasma from whole blood.

BACKGROUND

Many in vitro diagnostic testing systems and protocols require the use of blood specimens that are free of blood cells in order to perform a diagnostic test. These diagnostic tests either use serum or plasma which is separated from whole blood using techniques such as centrifugation or filtration.

Serum can be separated from whole blood by first allowing the blood to clot and then centrifuging the specimen to move all the blood cells to the bottom of the specimen tube. Plasma can be separated from whole blood by first mixing the whole blood with an anticoagulant such as lithium heparin or potassium EDTA and then centrifuging the specimen to move all the blood cells to the bottom of the specimen tube.

When using centrifugation to separate serum or plasma from whole blood, it is common to use a specimen tube that contains a thixotropic gel which has a greater specific gravity than serum or plasma, but lower specific gravity than blood cells. During centrifugation, this gel migrates above the blood cells while staying below the serum or plasma. The function of the gel is to provide a barrier between the serum or plasma and the blood cells so that the serum or plasma do not remix with the blood cells after centrifugation.

One difficulty of using serum or plasma from centrifuged specimen tubes is that it is difficult to extract serum or plasma from the specimen tube without leaving a large dead volume. The term "dead volume" refers to the amount of unusable sample left in the specimen tube after the maximum amount of sample has been extracted. When using an automated or manual pipette to extract sample from a centrifuged specimen tube, there is a risk that the pipette will make contact with either the blood cells or the gel separator. If this occurs, the sample may be disturbed remixing the blood cells and serum or plasma, the pipette may get clogged, or the pipette may not extract pure serum or plasma. To avoid these risks, the pipette must be kept a safe depth above the blood cells or gel separator to ensure it does not make contact with the blood cells or the gel separator. For an automated pipette, this means that the pipette depth is controlled such that the pipette tip keeps a safe distance from the blood cells or the gel separator. For a manual pipette, this means that the user exercises caution to keep the pipette a safe distance from the blood cells or the gel separator. The serum or plasma which is above the blood cells or the gel separator yet below the pipette tip is unusable as it won't be extracted in the pipette.

Leaving a large dead volume may not be problematic when the amount of serum or plasma available is significantly greater than the amount required by the diagnostic tests. However, as the amount of serum or plasma required by the diagnostic tests approaches the amount of serum or plasma available, dead volume becomes a greater concern. This is particularly important when using small volume sample collection technologies or in pediatric samples where the amount of blood able to be drawn is more limited.

In cases where it is not possible to collect larger amounts of a blood specimen, one common technique to reduce the dead volume left when pipetting from a centrifuged specimen container is to pour the serum or plasma out of the centrifuged specimen tube, into a secondary specimen tube. Because the secondary specimen tube does not contain blood cells or gel separator, a pipette can safely dive to the bottom of the specimen tube and the serum or plasma can be extracted with a low dead volume. While this technique results in a low dead volume, there are several significant disadvantages. This technique consumes an additional specimen container, which results in added material costs. The step of pouring serum or plasma increases labor costs and introduces risk of human error. There is also a risk of specimen mix-up if the new specimen tube is not properly labeled.

In order to, inter alia, make a blood draw less invasive and decrease the costs of the running diagnostic tests, many companies are currently developing specimen collection and processing techniques based on smaller sample volumes than are collected by most labs today. In order to effectively run diagnostic tests using serum or plasma collected in small volumes, approaches are needed to minimize the loss of serum or plasma due to dead volume. This invention enables diagnostic laboratories to effectively run diagnostic tests using smaller blood specimens or run more tests with the same volume of blood specimen.

SUMMARY

Provided herein is a device for separating serum or plasma from blood cells in a whole blood specimen. The present invention uses a cap with a reservoir, such that blood cells are packed into the cap when a specimen tube is centrifuged with the capped end away from the axis of centrifugation. When the cap is removed, the blood cells are also removed, so that the serum or plasma is left in the specimen tube where it can be readily extracted by a pipette which is able to reach all the way to the bottom of the specimen tube minimizing the dead volume.

BRIEF DESCRIPTION OF THE DRAWINGS

FIG. 1A-1C show a cross-sectional view of the specimen tube and cap according to the invention.

FIG. 3A-3I depicts the methodology for separating serum or plasma from blood cells according to the invention.

DETAILED DESCRIPTION OF ILLUSTRATIVE EMBODIMENTS

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise.

The term "about" as used herein when referring to a measurable value such as an amount and the like, is meant to encompass variations of up to +30% from the specified value, as such variations are appropriate to perform the disclosed methods. Unless otherwise indicated, all numbers expressing quantities of properties such as volume and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Figure 1C:
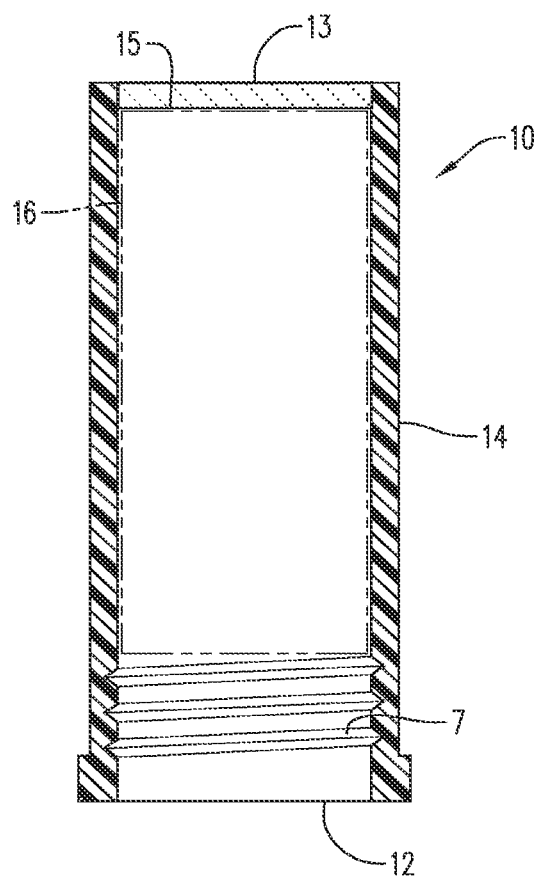

FIG. 1 depicts a specimen tube, often called a test tube, in which a blood specimen is collected according to the present invention. The specimen tube 1 has a closed end 3, open end 4 and lateral wall(s) 2. The open end 4 enables a liquid specimen to be inserted into the specimen tube 1. The closed end 3 is shown in a preferred embodiment with a round bottom. Specimen tubes having a round or conical bottom are preferred as they minimize dead volume when pipetting from the bottom of the specimen tube. While specimen tubes with round or conical bottoms are preferred, the bottom of the specimen tube can be any shape.

Figure 2:
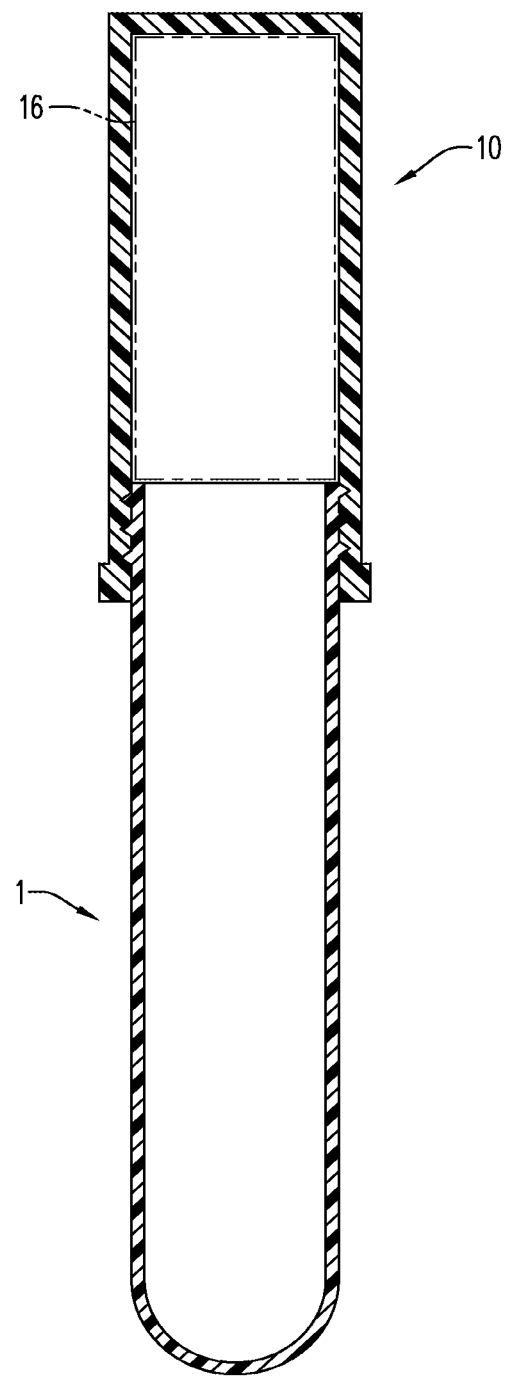
FIG. 2 shows a cross-sectional view of the specimen container according to the invention.

FIG. 1B depicts a cap 10 to secure onto a specimen tube such as that shown in FIG. 1A. The cap 10 has an open end 12, a closed end 13 and a lateral wall 14. The closed end 13 is closed by a surface 15. The cap 10 has a reservoir 16 which is formed when the cap 10 and specimen tube 1 are secured to formed a specimen container comprising the specimen tube and the cap, as shown in FIG. 2, where the volume of the reservoir 16 is defined as the maximum amount of liquid that can be contained in the cap 10 without coming into contact with the specimen tube 1. In order to remove the blood cells or other solids in the blood from the serum or plasma in accordance with the present invention, the volume of the reservoir 16 should be equal to or greater than the volume of the blood cells and other solids to be separated from the serum or plasma in the blood specimen. This will enable to the blood cells and other solids to be removed when the cap 10 is removed from the specimen tube 1. In another embodiment, the cap is sized so that volume of the reservoir is equal to or greater than the volume of whole blood in the specimen tube. This design will decrease or eliminate the pressure on the seal between the specimen tube and the cap during centrifugation.

The specimen tube 1 and cap 10 have a mechanism by which the open end 4 of the specimen tube 1 may be secured with the open end 12 of the cap 10 to form a specimen container, such that the blood specimen is contained within the specimen tube 1 and the cap 10. The mechanism for securing the specimen tube 1 and the cap 10 can be any mechanism desired as long as the specimen tube and cap are secured to create a leak free fitting. It is important that the contents of the specimen container do not leak when the specimen container is oriented in any direction. Such mechanisms for securing the specimen tube to the cap can include an engineered fit or interference fit. A preferred engineered fit is a threaded connection 7 where the specimen tube and the cap both have screw threads that work to connect the specimen tube and the cap together as shown in the figures. Any other engineered fit can be used that creates a leak free locking mechanism. Alternatively, an interference fit can be used such that the specimen tube and the cap are secured by friction after the open end of the specimen tube and open end of the cap are pushed together. For example, the cap can be a plug that is secured onto the open end of the specimen tube. Optionally, the joint between the specimen tube and the cap can be sealed using a gasket. The mechanism to secure the specimen tube and cap together is not limited to any particular mechanism and shall include any mechanism whereby the specimen tube and cap can be secured together to create a leak free specimen container.

FIGS. 3A-3I depict an embodiment of the inventive method to separate serum or plasma from a blood specimen and works as follows:

In FIG. 3A an empty specimen tube 20 having a closed end 21, open end 22 and lateral wall(s) 23 is shown. FIG. 3B shows the specimen tube 20 filled with a whole blood specimen 24 which was inserted through open end 22. In FIG. 3C, a cap 30, such as that shown in FIG. 1B, is secured to the open end 22 of the specimen tube 20. A specimen tube that is enclosed with a cap is referred to herein as a specimen container. The cap has an open end 32, a closed end 33 and a lateral wall 34. The cap 30 contains a separator 31.

For purposes of this invention, a separator is a device that is put into a specimen tube (or alternatively, into a cap) in order to ensure that after the specimen tube is centrifuged, there is a physical layer separating the serum or plasma from the blood cells and other solids. The separator is chosen such that it has a higher specific gravity than serum and/or plasma and lower specific gravity than blood cells and other solids in the blood to be removed. During centrifugation, the serum or plasma is separated from blood cells and any other solids in the blood by migrating closer to the axis of centrifugation because it has lower specific gravity. The blood cells (and other solids) migrate further away from the axis of centrifugation because they have higher specific gravity. The separator migrates to a level between the serum or plasma and the blood cells (and other solids), because it has intermediate specific gravity. The primary function of the separator is to maintain the purity of the serum or plasma by 1) preventing the serum or plasma from remixing with the blood cells, and 2) preventing the serum or plasma from becoming contaminated by the blood cells as they degrade.

A preferred separator is a thixotropic gel. This is a hydrophobic gel which is initially solid, but becomes liquefied during centrifugation so that it can migrate to form a layer between the serum or plasma and the blood cells (and other solids). A preferred thixotropic gel is a polyester based formulation, however any thixotropic gel can be used. Other nonlimiting examples are a mixture of silicon fluid and a hydrophobic powdered silica or a mixture of a hydrocarbon polymer and a powdered silica. Another preferred embodiment uses a thixotropic gel which is UV-curable in order to improve the strength of the barrier that is formed between the serum or plasma and the blood cells and other solids. Alternative types of separators include mechanical separators (e.g. elastomer barriers such as used in BD Barricor technology) and filter-based separators.

In the preferred embodiment shown in FIG. 3A-3I, the separator 31 is a thixotropic gel. In FIG. 3D, the specimen container is centrifuged while oriented such that the closed end 33 of the cap 30 is further away from the axis of centrifugation 38 than the closed end 21 of the specimen tube 20. During centrifugation, blood cells 40 and any other solids that have a greater specific gravity than serum or plasma migrate to the reservoir 35. FIG. 3E shows the specimen container after it is centrifuged while oriented (in this case shown in an inverted orientation) so that the blood cells 40 migrate toward the closed end 33 of the cap 30 and into the reservoir 35. Due to the difference in specific gravity, the thixotropic gel separator 31 migrates above the blood cells 40 and forms a layer between the serum or plasma 42 and the blood cells 40. The serum or plasma 42 migrates above the thixotropic gel separator 31. In Figure F, the specimen container is orientated upright with the cap 30 above the specimen tube 20 such that gravity moves the serum or plasma 42 to the closed end 21 of the specimen tube 20. The thixotropic gel separator 31 remains in the cap 30 of the specimen container and keeps the blood cells 40 trapped within the cap 30. In FIG. 3G, the cap 30 is removed from the specimen tube 20. The blood cells 40 and thixotropic gel separator 31 are also removed because they are contained within in the reservoir 35. The serum or plasma 42 is retained in the specimen tube 20. In FIG. 3H, a pipette 50 is inserted into the specimen tube 20 to extract the serum or plasma 42. Because there are no blood cells and no separator in the specimen tube, the pipette is able to safely descend to the bottom of the specimen tube to extract the serum or plasma without risk of contacting any of the separator or blood cells. In FIG. 3I, the pipette has extracted nearly all of the serum or plasma, while leaving a very small unusable dead volume. The conventional method of separating serum or plasma from whole blood leaves the blood cells and separator at the bottom of the specimen tube, which results in significantly higher dead volume because the pipette must keep a safe distance from the separator and blood cells to ensure there is no contact. The invention achieves having a significantly smaller dead volume, without incurring the added cost and risk of pouring the serum or plasma into a secondary specimen tube.

An important element of the present invention is the cap design, which includes a reservoir large enough to contain the blood cells from the specimen along with any other solids or separator to be removed. The advantage of containing and capturing blood cells, other solids and any separator within the cap is that when the cap is removed, the blood cells and any other solids or separator are removed with the cap, leaving only serum or plasma in the specimen tube to be pipetted.

Another important element of the present invention is the technique of centrifuging the specimen container while oriented with the closed end of the cap further away from the axis of centrifugation than the closed end of the specimen tube. Centrifuging the specimen container with the closed end of the cap further way from the axis of centrifugation than the closed end of the specimen tube captures the blood cells, other solids and any separator in the reservoir in the cap. This enables the blood cells, other solids and any separator to be removed from the specimen when the cap is removed after centrifugation leaving just the serum or plasma in the specimen tube to be extracted for testing.

Figure 4A:
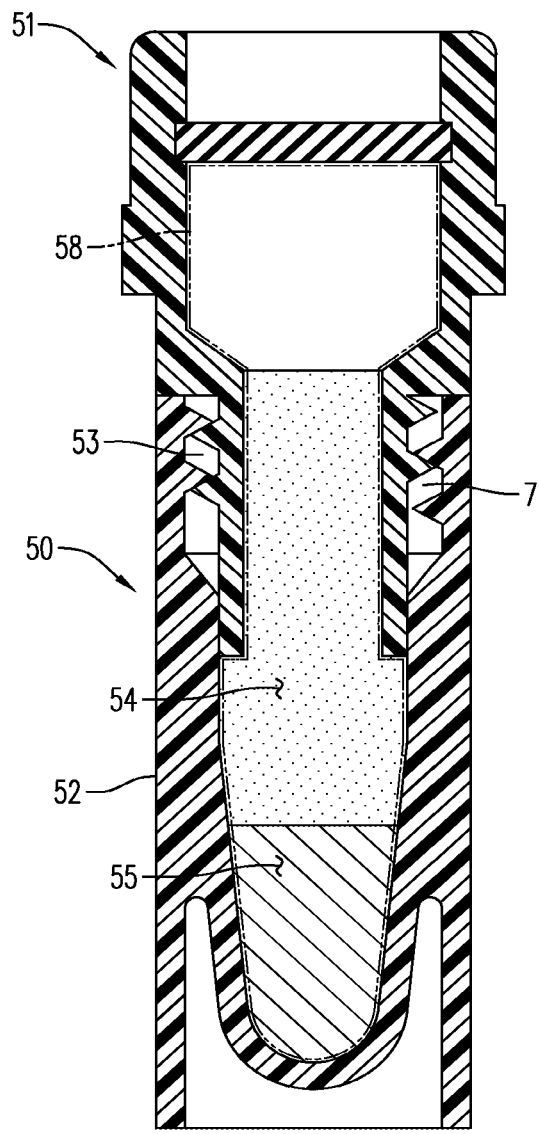
FIGS. 4A and 4B depicts a preferred embodiment of the specimen container according to the present invention.
Figure 4B:
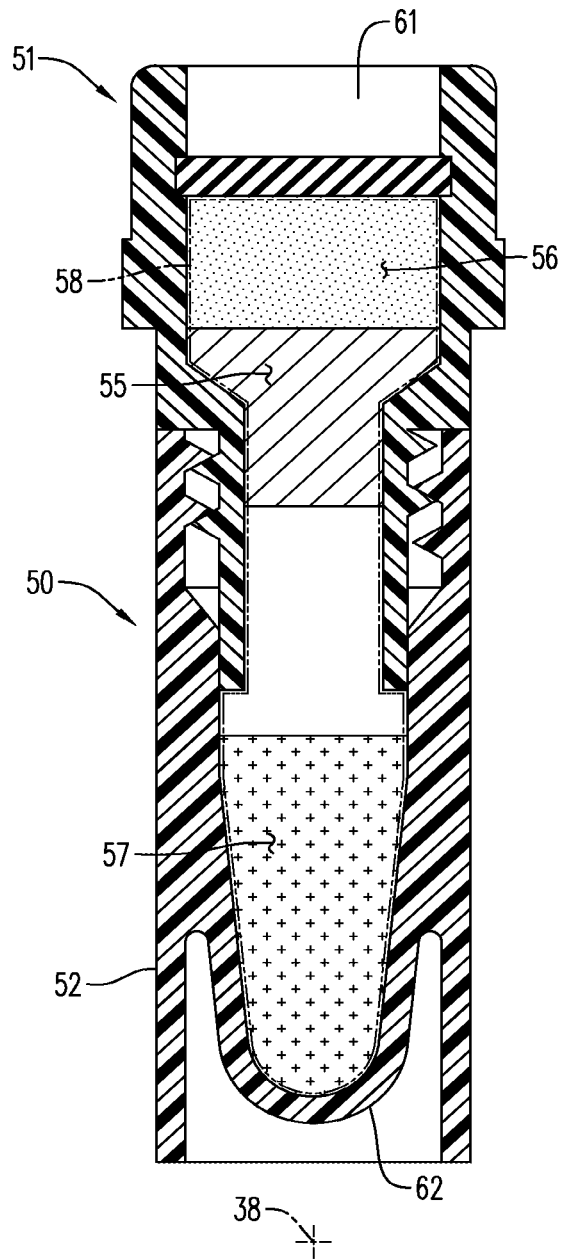

FIGS. 4A and 4B depict a preferred embodiment of the present invention. FIG. 4A depicts a sample container 50 with cap 51 secured to sample tube 52. The cap 51 is secured by threaded connection 53 which secures to the internal threading of the sample tube 52. In this embodiment, the cap 51 is structured such that the reservoir 58 extends into the sample tube 52. The sample container 50 contains a whole blood specimen 54 and a thixotropic gel 55 as a separator. FIG. 4A depicts the sample container prior to centrifugation. FIG. 4B depicts the sample container after centrifugation and shows the blood cells and other solids 56 separated from the serum or plasma 57 by the thixotropic gel 55 which acts as a separator. The sample container was centrifuged with the closed end 61 of the cap 51 further away from the axis of centrifugation 38 than the closed end 62 of the specimen tube 52 so that the components of greater specific gravity (i.e. blood cells and any other solids to be removed from the whole blood specimen) moved to the closed end 61 of the cap 51. The thixotropic gel 55 separator which has a specific gravity intermediate to that of the blood cells and serum or plasma forms a layer between the blood cells and any other solids to be removed and the serum or plasma. The cap 51 can then be removed leaving only serum or plasma contained in the specimen tube.

While particular embodiments of the invention have been described and illustrated, it is not intended that the invention be limited thereto. It is intended that the invention be as broad in scope as the art will allow and that the disclosure herein be interpreted likewise.

FIG. 1A shows a cylindrical specimen tube as is typically used to collect blood specimens, however the specimen tube need not be cylindrical in shape. The invention could apply to specimen tubes with any shape desired.

FIGS. 1A-B, 2, 3A-I, and 4A-B do not show the dimensions of the specimen container. Due to the applicability to small sample volumes, the size of the specimen container is preferably a micro-sample tube in the range of 0.1 mL to 2.0 mL. However, the invention is also applicable to larger conventional specimen tubes in the range of 2.0 mL to 10.0 mL or greater. The invention is not specific to any particular dimension of specimen container and can be applied to specimen tubes of any size.

FIG. 1A shows the use of a specimen tube having a round closed end. This is a preferred embodiment because this geometry minimizes the dead volume for a conventional pipette. The invention is not specific to any particular shape of specimen tube or specimen container and can be applied to specimen tubes or specimen containers of any shape.

FIG. 3B shows whole blood added to the specimen container while there is no cap on the specimen container. An alternate approach would be to add blood to the specimen container while the cap is attached. In this embodiment, the closed end of the cap would contain a pierceable material such that a cannula can be inserted through the closed end of the cap to insert a blood specimen into the specimen container. The pierceable material would need to be such that it will reseal so that the specimen container does not leak the blood specimen contained within. This is commonly done today using evacuated specimen tubes that have a cap with a septum that can be pierced with a needle. In such an embodiment, cap surface 15 in FIG. 1C or at least part thereof would be made up a material capable of being punctured with a needle. The material should be self-sealable such that after it is punctured with a needle, it will reseal so that the specimen does not leak out of the cap.

This embodiment shall also embody any configuration wherein the closed end of the cap can be unsealed and resealed such that a cannula can insert blood through the closed end of the cap.

In another preferred embodiment, the volume inside the specimen container is evacuated. This causes the blood specimen to be pulled into the specimen container by air pressure.

The figures show the specimen container and cap having a screw-type connection in order to connect the cap to the top end of the specimen container. A screw-type connection is the preferred embodiment as it provides the most secure seal for centrifugation. However, the cap may be attached to the specimen container by a variety of methods. A few examples are provided but the invention should not be limited to the examples and should include any method for securing the cap to the specimen container. A stopper-type connection may be used, but extra sealing pressure may be required to be applied during centrifugation. A gasket between the tube and the cap may be useful in such an embodiment to improve the seal.

The preferred embodiment described and illustrated show the specimen tube and cap as standalone components. In another embodiment, the cap may be physically tethered to the specimen container so that they are always connected. Once the blood specimen is centrifuged to separate the serum or plasma from the blood cells and other solids, the cap should be able to be opened such that a pipette is able to be inserted into the specimen tube to pipette the serum or plasma or such that the serum or plasma can be poured out into a separate container such as a different specimen tube.

An alternative embodiment is to integrate the cap into another device. For example, a blood collection device with a threaded opening could act as the cap for a specimen tube. This blood collection device could have a dual function where it puts blood into the specimen tube and also acts as the cap.

An alternative embodiment is to have a single device which functions as multiple caps. For example, a single plastic device with multiple threaded openings could act as the cap for multiple specimen tubes, with each threaded opening having its own reservoir. What is essential is that each threaded opening, which acts as a cap, contains a reservoir large enough to hold the blood cells and any other solids or separator.

An alternative embodiment is to have a single device which functions as multiple specimen tubes. For example, a multi-well plate could act as multiple specimen tubes, with each well in the plate capable of being secured by a cap which contains a reservoir.

The preferred embodiments described and illustrated in FIGS. 3A-3I, 4A and 4B include the use of a thixotropic gel as a separator gel. This design is preferred as the gel provides a reliable barrier to prevent the blood cells from remixing with the serum or plasma. An alternative is to not use any separator and rely on the centrifugation to pack the blood cells tightly enough in the reservoir such that they remain in the cap after centrifugation and when the cap is removed.

FIG. 3C shows the separator (e.g. a thixotropic gel) initially contained in the cap. This embodiment is preferred because it allows the specially designed cap to be used with commodity specimen tubes which do not contain a separator (e.g. a thixotropic gel). An alternative embodiment is to have the separator gel (e.g. a thixotropic gel) initially contained in the specimen tube.

FIG. 3E shows that the size of the reservoir has been designed such that the maximum volume it can hold is the volume of blood cells plus the volume of the separator gel. This minimizes the size of the cap while still ensuring that the blood cells and separator gel will be fully contained within the cap. The cap must be of sufficient size so that the reservoir has a volume sufficient to hold the volume of blood cells plus the volume of any other solids such as the separator. An alternative embodiment is to size the reservoir such that its volume is equal to or greater than the specimen tube's volume. This would ensure that during centrifugation there is no pressure on the seal between the specimen tube and the cap.

The preferred embodiment described and illustrated describe the separation of serum or plasma from whole blood. This implies the possible use of chemical additives to the whole blood. For instance, to separate serum, a clot activator such as silica may be used. To separate plasma, an anticoagulant such as lithium heparin or potassium EDTA can be used. This invention is not limited to the use of any particular additive.

What is claimed:

1. A specimen container for separating plasma or serum from blood cells in a blood sample, the specimen container including:
 a cylindrical specimen tube having a closed end, an open end, and defining an inner volume therebetween, the closed end being at least one of round or conical, the open end being the only opening of the specimen container tube, the specimen tube configured to receive the blood sample through the open end of the specimen tube; and
 a cap defining a reservoir having a maximum cross-sectional area greater than a maximum cross-sectional area of the inner volume of the specimen tube, the cap configured to be rotatably coupled to the specimen tube to enclose the inner volume and place the inner volume in fluid communication with the reservoir, the cap configured to accommodate delivery of the blood sample therethrough when the cap is coupled to the specimen tube and then become sealed,
 the specimen container configured to be centrifuged with the cap further away from an axis of centrifugation than the closed end of the specimen tube such that blood cells in the blood sample migrate into the reservoir and remain in the reservoir after the specimen container is centrifuged,
 the cap, with the blood cells disposed within the reservoir, being rotatably removable from the specimen tube to expose the open end of the specimen tube such that serum or plasma from the blood sample can be withdrawn through the open end of the specimen tube.

2. The specimen container of claim 1, wherein the reservoir extends into the specimen tube when the cap is coupled to the specimen tube.

3. The specimen container of claim 2, wherein the specimen tube includes a coupling feature disposed on an inside surface of the specimen tube, and the cap includes a coupling feature disposed on an outside surface of the cap configured to be rotatably coupled to the coupling feature of the specimen tube.

4. The specimen container of claim 1, wherein the cap has a closed end including a pierceable material, the pierceable material configured such that a cannula can be inserted through the closed end of the cap.

5. The specimen container of claim 1, wherein the inner volume of the specimen tube is about 0.1 mL to about 2.0 mL.

6. The specimen container of claim 1, wherein a volume of the reservoir is greater than or equal to the inner volume of the specimen tube.

7. The specimen container of claim 1, wherein the specimen tube includes a coupling feature disposed on an outside surface of the specimen tube, and the cap includes a coupling feature disposed on an inside surface of the cap, the coupling feature of the cap configured to be rotatably coupled to the coupling feature of the specimen tube to enclose the inner volume and place the inner volume in fluid communication with the reservoir.

8. The specimen container of claim 1, wherein a portion of the cap circumferentially surrounds a portion of the specimen tube when the cap is coupled to the specimen tube.

9. The specimen container of claim 1, further comprising:
a separator disposed in at least one of the inner volume or the reservoir, the separator configured to migrate into the reservoir and remain in the reservoir after the specimen container is centrifuged.

10. The specimen container of claim 9, wherein the separator includes at least one of a thixotropic gel, a mechanical separator, or a filter-based separator.

11. A specimen container for separating serum or plasma from blood cells in a blood sample, the specimen container comprising:
a cylindrical specimen tube having a closed end, an open end, and defining an inner volume therebetween, the closed end being at least one of round or conical, the open end being the only opening of the specimen tube, the specimen tube including a coupling feature disposed on an outside surface of the specimen tube, the specimen tube configured to receive the blood sample through the open end of the specimen tube; and
a cap defining a reservoir having a maximum cross-sectional area greater than a maximum cross-sectional area of the inner volume of the specimen tube, the cap including a coupling feature disposed on an inside surface of the cap and configured to be rotatably coupled to the coupling feature of the specimen tube to enclose the inner volume and place the inner volume in fluid communication with the reservoir, the cap configured to accommodate delivery of the blood sample therethrough when the cap is coupled to the specimen tube and then become sealed,
the specimen container configured to be centrifuged with the cap further away from an axis of centrifugation than the closed end of the specimen tube such that blood cells in the blood sample migrate into the reservoir and remain in the reservoir after the specimen container is centrifuged,
the cap, with the blood cells disposed within the reservoir, being removable from the specimen tube to expose the open end of the specimen tube such that serum or plasma from the blood sample can be withdrawn through the open end of the specimen tube.

12. The specimen container of claim 11, wherein the closed end of the cap includes a pierceable material configured such that a cannula can be inserted through the closed end of the cap.

13. The specimen container of claim 11, wherein the inner volume of the specimen tube is about 0.1 mL to about 2.0 mL.

14. The specimen container of claim 11, wherein a volume of the reservoir is greater than or equal to the inner volume of the specimen tube.

15. The specimen container of claim 11, further comprising:
a separator disposed within at least one of the inner volume or the reservoir, the separator configured to migrate into the reservoir and remain in the reservoir after the specimen container is centrifuged.

16. The specimen container of claim 15, wherein the separator includes at least one of a thixotropic gel, a mechanical separator, or a filter-based separator.

17. The specimen container of claim 11, wherein a portion of the cap circumferentially surrounds a portion of the specimen tube when the cap is coupled to the specimen tube.

18. A specimen container for separating serum or plasma from blood cells in a blood sample, the specimen container comprising:
a cylindrical specimen tube having a closed end, an open end, and defining an inner volume therebetween, the closed end being at least one of round or conical, the open end being the only opening of the specimen tube, the specimen tube including a coupling feature disposed on an outside surface of the specimen tube, the specimen configured to receive the blood sample through the open end of the specimen tube; and
a monolithic cap defining a reservoir, the reservoir having a maximum cross-sectional area greater than a maximum cross-sectional area of the inner volume of the specimen tube, the monolithic cap including a coupling feature disposed on an inside surface of the monolithic cap and configured to be rotatably coupled to the coupling feature of the specimen tube to enclose the inner volume and place the inner volume in fluid communication with the reservoir, a portion of the monolithic cap circumferentially surrounds a portion of the specimen tube when the monolithic cap is coupled to the specimen tube, the monolithic cap configured to accommodate delivery of the blood sample therethrough when the monolithic cap is coupled to the specimen tube and then become sealed,
the specimen container configured to be centrifuged with the monolithic cap further away from an axis of centrifugation than the closed end of the specimen tube such that blood cells in the blood sample migrate into the reservoir and remain in the reservoir after the specimen container is centrifuged,
the monolithic cap, with the blood cells disposed within the reservoir, being removable from the specimen tube to expose the open end of the specimen tube such that serum or plasma from the blood sample can be withdrawn through the open end of the specimen tube.

19. The specimen container of claim 18, wherein the monolithic cap has a closed end including a pierceable material configured such that a cannula can be inserted through the closed end of the monolithic cap.

20. The specimen container of claim 18, wherein the inner volume of the specimen tube is about 0.1 mL to about 2.0 mL.

21. The specimen container of claim 18, wherein a volume of the reservoir is the same as or greater than the inner volume of the specimen tube.

22. The specimen container of claim 18, further comprising a separator disposed within at least one of the inner volume or the reservoir, the separator configured to migrate into the reservoir and remain in the reservoir after the specimen container is centrifuged.

23. The specimen container of claim 22, wherein the separator includes at least one of a thixotropic gel, a mechanical separator, or a filter-based separator.

* * * * *